(12) United States Patent
Le Berre et al.

(10) Patent No.: US 6,916,952 B1
(45) Date of Patent: Jul. 12, 2005

(54) METHOD FOR PREPARING ACETIC ACID AND OR METHYL ACETATE IN THE PRESENCE OF IRIDIUM AND PLATINUM

(75) Inventors: Carole Le Berre, La Croix-Falfgarde (FR); Philippe Kalck, Auzeville-Tolosane (FR); Philippe Serp, Toulouse (FR); Lise Layeillon, Lacq (FR); Daniel Thiebaut, Lescar (FR)

(73) Assignee: Acetex Chimie, Neuilly sur Seine Cedex (FR)

( * ) Notice: Subject to any disclaimer, the term of this patent is extended or adjusted under 35 U.S.C. 154(b) by 0 days.

(21) Appl. No.: 09/807,434

(22) PCT Filed: Oct. 29, 1999

(86) PCT No.: PCT/FR99/02652

§ 371 (c)(1),
(2), (4) Date: Apr. 23, 2001

(87) PCT Pub. No.: WO00/27785

PCT Pub. Date: May 18, 2000

(30) Foreign Application Priority Data

Nov. 5, 1998 (FR) .......................... 98 13954

(51) Int. Cl.$^7$ .......................... C07C 67/36; C07C 51/12
(52) U.S. Cl. .......................... 560/232; 562/519
(58) Field of Search .......................... 560/129, 231; 562/400, 512, 517, 519

(56) References Cited

FOREIGN PATENT DOCUMENTS

| FR | 2750985 | 1/1998 |
| GB | 1234641 | 6/1971 |
| WO | 9735828 | 10/1997 |
| WO | 9833759 | 8/1998 |

*Primary Examiner*—Johann Richter
*Assistant Examiner*—Karl Puttlitz
(74) *Attorney, Agent, or Firm*—Dennison, Schultz, Dougherty & MacDonald

(57) ABSTRACT

The invention relates to a process for the preparation of acetic acid and/or methyl acetate in the liquid phase by the carbonylation of methanol and/or the isomerization of methyl formate in the presence of water, a solvent, a homogeneous catalyst system comprising iridium and a halogen-containing promoter, and carbon monoxide, wherein said catalyst system also comprises platinum.

54 Claims, No Drawings

METHOD FOR PREPARING ACETIC ACID AND OR METHYL ACETATE IN THE PRESENCE OF IRIDIUM AND PLATINUM

BACKGROUND OF THE INVENTION

The present invention relates to a process for the preparation of acetic acid and/or methyl acetate in the liquid phase in the presence of a homogeneous catalyst comprising iridium and platinum.

The process of the invention makes it possible to obtain an increased productivity in terms of acetic acid, as well as an improved stability of the catalyst system employed.

Various ways of obtaining acetic acid are known and exploited in industry. These include the methanol carbonylation reaction carried out in the liquid phase, under a pressure of carbon monoxide, which is one of the reactants, in the presence of a homogeneous catalyst system. Another way of obtaining acetic acid consists in isomerizing methyl formate. This reaction, too, is generally carried out in the presence of a catalyst system in the homogeneous phase. Finally, another process involves carrying out the carbonylation of methanol and the isomerization of methyl formate simultaneously.

More precisely, the carbonylation process using rhodium is a known process, exploited in industry, which has formed the subject of numerous articles and patents, for example American patents U.S. Pat. No. 3,769,329 and U.S. Pat. No. 3,813,428.

European patents EP 618 183 and EP 618 184, and European patents EP 785 919 and EP 759 022, describe a carbonylation process carried out in the presence of a catalyst system based on iridium and, if appropriate, also containing rhodium.

A carbonylation process using iridium and ruthenium, which is currently exploited in industry, is described in European patent EP 643 034.

More recently, a new preparative process, consisting of a methyl formate isomerization reaction in the presence of iridium, was proposed in French patent FR 2 746 794 and international patent application WO 97/135829.

In parallel, a process for the preparation of acetic acid and/or methyl acetate by carrying out a methyl formate isomerization reaction and a methanol carbonylation reaction simultaneously was proposed in patent FR 2 746 795 and international patent application WO 97/35828.

These different processes for acetic acid production are generally carried out continuously in plants comprising essentially three zones. The first corresponds to the actual reaction zone comprising a pressurized reactor in which the carbonylation and/or isomerization are carried out. The second consists of a zone for separation of the acid formed. This operation is effected by partial vaporization of the reaction mixture in a so-called flash apparatus, in which the pressure is kept below that in the reactor. The vaporized part is then sent to a third zone, where the acetic acid produced is purified. This zone comprises various distillation columns in which the acetic acid produced is separated from the water, the reactants and the by-products. That part of the mixture which remains in liquid form at the outlet of the vaporization zone, and comprises especially the catalyst, is recycled to the reactor.

SUMMARY OF THE INVENTION

The aim of the process according to the invention is to improve the processes described above by using a homogenous phase catalyst system comprising iridium and platinum.

In fact, it has now been found that the addition of platinum to a catalyst system based on iridium or iridium and rhodium makes it possible, totally unexpectedly, to increase the acid production rate. In other words, the process according to the invention makes it possible to achieve a reaction rate which is greater than or equal to that obtained, under the same conditions, with a catalyst system involving only iridium or an iridium/rhodium mixture, while the total number of moles of metals used in the process of the invention remains unchanged.

Apart from the productivity increase, obtaining comparable rates using a smaller number of moles of catalyst constitutes an additional economic advantage, namely that of reducing the catalyst costs.

It has also been shown that platinum considerably enhances the stability of the iridium, even when the water content is low.

DETAILED DESCRIPTION OF THE INVENTION

The process according to the invention is carried out in the liquid phase. Consequently the catalyst system used is in a form soluble in the reaction medium.

The catalyst system suitable for carrying out the invention is based on at least one iridium compound, by itself or in the presence of rhodium, and at least one halogen-containing promoter and also comprises at least one platinum derivative.

Thus, according to one of its essential characteristics, the invention relates to a process for the preparation of acetic acid and/or methyl acetate in the liquid phase by the carbonylation of methanol and/or the isomerization of methyl formate in the presence of water, a solvent, a homogeneous catalyst system comprising iridium and a halogen-containing promoter, and carbon monoxide, wherein said catalyst system also comprises platinum.

The invention therefore consists in improving the processes for the preparation of acetic acid by isomerization, by carbonylation or by a combination of isomerization and carbonylation by using a catalyst system based on soluble iridium and a halogen-containing promoter, and by adding platinum to said catalyst system in a form soluble in the medium.

In a first variant of the process of the invention, methanol is carbonylated by maintaining a carbon monoxide partial pressure of between $0.1.10^5$ Pa and $200.10^5$ Pa throughout the reaction.

In a second variant of the process, methyl formate is isomerized by maintaining a carbon monoxide partial pressure of between $0.1.10^5$ Pa and $25.10^5$ Pa throughout the reaction. The preferred conditions for carrying out such a process can be obtained directly by those skilled in the art by reference to international patent application WO 97/35829 cited above, except that platinum is added to the iridium.

In a third variant of the process, a methanol carbonylation reaction and a methyl formate isomerization reaction are carried out simultaneously by maintaining a carbon monoxide partial pressure of between $0.1.10^5$ Pa and $25.10^5$ Pa throughout the reaction. The preferred conditions for carrying out such a process can be obtained directly by those skilled in the art by reference to international patent application WO 97/35828 cited above, except that platinum is added to the iridium In the catalyst system used in the above three variants, the iridium may advantageously be replaced with a combination of iridium+rhodium.

In cases where a catalyst system containing rhodium is employed, the atomic ratio of rhodium to iridium may vary within wide limits, i.e. between 0.01 and 99.

In all these variants, the platinum will be introduced into the reaction medium in a sufficient amount and in appropriate proportions relative to the iridium. Experiments carried out by the inventors of the present invention have in fact shown that the optimum amounts and proportions of platinum are intimately associated with the form in which the platinum is introduced into the reaction medium.

In precise terms, it is possible to use any platinum compounds which are soluble or capable of being solubilized in the reaction medium under the conditions of the invention.

As examples, and without implying a limitation, the following are particularly suitable for carrying out the invention:

platinum compounds hereafter referred to as "simple compounds", such as platinum in the metallic state, its salts and its oxides; and coordination complexes of this metal.

The compounds in the form of complexes prove to be the preferred compounds according to the invention.

The salts used are preferably platinum halides. The halogen is more particularly selected from chlorine, bromine and iodine, the last of these being preferred.

Thus compounds such as $PtI_2$, $PtBr_2$, $PtCl_2$, $PtCl_4.xH_2O$, $H_2PtCl_6.xH_2O$, $Na_2PtCl_4.xH_2O$ and $Na_2PtCl_6.xH_2O$ can be used in the process according to the invention.

Oxides, selected from $PtO$, $PtO_2$ and $PtO_2.xH_2O$, can likewise be appropriately used in the process according to the invention.

As far as the soluble platinum coordination complexes are concerned, the most commonly used compounds are those having ligands selected from carbon monoxide and a carbon monoxide/halogen combination, the halogen being selected from chlorine, bromine and, more particularly, iodine. It is not excluded, however, to use soluble platinum complexes whose ligands are selected for example from organophosphorus and organonitrogen compounds.

The following compounds may be mentioned, without implying a limitation, as coordination complexes which are known to those skilled in the art and are particularly suitable for carrying out the invention: $PtI_2(CO)_2$, $[PtI_2(CO)]_2$, $[Pt_3(CO)_6]^{2-}[Q^+]_2$ and $[Pt_6(CO)_{12}]^{2-}[Q^+]_2$, in which formulae Q can be especially hydrogen or a group $NR_4$ or $PR_4$, where R is selected from hydrogen and/or a hydrocarbon radical, tetraiododicarbonyldiplatinum, $[PtI_2(CO)]_2$, being preferred.

In a first variant of the invention, if the platinum is introduced in the form of a simple compound—platinum in the metallic state, salts or oxides—it will be preferable to maintain a platinum content of at least 4 mmol/l of reaction medium and an atomic ratio of iridium to platinum of between 2 and 5.

In a second, particularly preferred variant of the invention, if the platinum is introduced in the form of a coordination complex of this metal with ligands selected from carbon monoxide, a carbon monoxide/halogen combination and organo-nitrogen and organophosphorus compounds, it will be preferable to maintain a platinum content of at least 1 mmol/l of reaction medium and an atomic ratio of iridium to platinum of between 1 and 5.

The atomic ratio of iridium to platinum or, in the case where the catalyst system also comprises rhodium, the atomic ratio of (iridium+rhodium) to platinum is between 2 and 5 when the platinum is used in the form of simple compounds as defined above, and between 1 and 5 when the platinum is introduced in the form of coordination complexes. The platinum content will preferably be at least 4 mmol/l of reaction medium in the case of simple platinum compounds and at least about 1 mmol/l in the case of coordination complexes.

In general, the concentration of iridium or, if appropriate, iridium+rhodium in the reaction medium is between 0.1 and 100 mmol/l, preferably between 1 and 20 mmol/l.

Any of the rhodium- and iridium-based compounds conventionally used in carbonylation and/or isomerization reactions can be employed in the process according to the invention.

It is possible to use any iridium compounds which are soluble or capable of being solubilized in the reaction medium under the operating conditions of the invention. As examples, and without implying a limitation, iridium in the metallic state, salts of this metal oxides or coordination complexes are particularly suitable for carrying out the invention.

The iridium salts conventionally used are iridium halides. The halogen is more particularly selected from chlorine, bromine and iodine, the last of these being preferred. Thus compounds like $IrI_3$, $IrBr_3$, $IrCl_3$, $IrI_3.4H_2O$, $IrI_4$ and $IrBr_3.4H_2O$ can be used in the process according to the invention.

Oxides, selected from $IrO_2$ and $Ir_2O_3.xH_2O$, can likewise be appropriately used in the process according to the invention.

As far as soluble iridium coordination complexes are concerned, the most commonly used compounds are those having ligands selected from carbon monoxide and a carbon monoxide/halogen combination, the halogen being selected from chlorine, bromine and, more particularly, iodine. It is not excluded, however, to use soluble iridium complexes whose ligands are selected for example from organophosphorus and organonitrogen compounds.

The following compounds may be mentioned, without implying a limitation, as coordination complexes which are known to those skilled in the art and are particularly suitable for carrying out the invention: $Ir_4(CO)_{12}$, $Ir(CO)_2I_2^-Q^+$, $Ir(CO)_2Br_2^-Q^+$ and $Ir(CO)_2Cl_2^-Q^+$, in which formulae Q can be especially hydrogen or a group $NR_4$ or $PR_4$, where R is selected from hydrogen and/or a hydrocarbon radical.

These catalysts can be obtained by any method known to those skilled in the art. Reference may thus be made to patents EP 657 386 and EP 737 103 for the preparation of iridium-based catalyst solutions suitable for carrying out the present invention.

As indicated previously, the reaction according to the invention can be carried out with a catalyst system comprising iridium by itself, or iridium and rhodium, in addition to platinum.

In general, the rhodium- and iridium-based compounds used are selected from coordination complexes of these metals which are soluble in the medium under the reaction conditions. More particularly, the coordination complexes used are those whose ligands are on the one hand carbon monoxide and on the other hand a halogen such as chlorine, bromine or, more particularly, iodine. It is of course possible to use soluble complexes comprising ligands other than those mentioned, such as organophosphorus or organonitrogen ligands in particular. Advantageously, however, the present invention does not require the use of rhodium and iridium complexes of this type.

Thus complexes of the type $Ir_4(CO)_{12}$, $Ir(CO)_2I_2^-Q^+$, $Ir(CO)_2Br_2^-Q^+$, $Rh_4(CO)_{12}$, $Rh(CO)_2I_2^-Q^+$ or $Rh(CO)_2Br_2^-Q^+$, or complexes based on both metals, such as $Rh_3Ir(CO)_{12}$ or $Rh_2Ir_2(CO)_{12}$, in which formulae Q can be especially hydrogen or a group $NR_4$ or $PR_4$, where R is selected from hydrogen and/or a hydrocarbon radical, may be mentioned especially as examples of coordination complexes which are used more particularly in the present invention.

Compounds selected from the salts of these elements, such as especially $IrI_3$, $IrBr_3$, $IrCl_3$, $IrI_3.4H_2O$, $IrBr_3.4H_2O$, $RhI_3$, $RhBr_3$, $RhCl_3$, $RhI_3.4H_2O$ and $RhBr_3.4H_2O$, or rhodium and iridium in the metallic state, can likewise be used in the process according to the invention.

It should be noted that the above-mentioned list of rhodium- and iridium-based compounds cannot be considered as exhaustive and that reference may be made to patents U.S. Pat. No. 3,769,329 and U.S. Pat. No. 3,772,380, whose teaching is included herewith, for additional examples of compounds of the two metals mentioned above.

In general, the rhodium-, iridium- and platinum-based compounds used are selected from the coordination complexes of these metals which are soluble in the medium under the reaction conditions. More particularly, the coordination complexes used are those whose ligands are on the one hand carbon monoxide and on the other hand a halogen such as chlorine, bromine or, more particularly, iodine. It is of course possible to use soluble complexes comprising ligands other than those mentioned, such as organophosphorus or organonitrogen ligands in particular. Complexes of two or three of the above metals may also be mentioned; $[PtRh_5(CO)_{15}]^-Q^+$, Q being as defined above, may be mentioned without implying a limitation.

One important characteristic of the invention lies in the fact that the platinum is present in the reaction medium in a sufficient amount and in appropriate proportions relative to the iridium. The platinum concentration is equal to at least 4 mmol/l of reaction medium and, in addition, the atomic ratio of iridium or (iridium+rhodium) to platinum is between 2 and 5 in the case where simple platinum compounds are used. If the platinum is introduced in the form of a coordination complex, the platinum concentration is preferably equal to at least 1 mmol/l of reaction medium and the atomic ratio of iridium to platinum is between 1 and 5. It has in fact been observed, totally unexpectedly, that such conditions allow a considerable increase in the reaction rate. Remarkably, the stability of the catalyst system is also appreciably improved under these conditions.

Apart from the compounds mentioned above, the catalyst system according to the invention comprises a halogen-containing promoter. This can take the form of a halogen by itself or a halogen combined with other moieties such as hydrogen or the methyl or acetyl radical.

The halogen is generally selected from chlorine, bromine and iodine, iodine being preferred.

Iodine, hydriodic acid, methyl iodide and acetyl iodide may be mentioned as halogen compounds which can also be used as promoters.

Methyl iodide will preferably be used as the halogen-containing promoter.

In one variant of the invention, the halogen-containing promoter is partially or totally introduced into the reaction mixture in the form of a precursor. In such a case, said precursor generally takes the form of a compound which is capable of releasing the hydrocarbon radical of the above-mentioned halogen-containing promoter into the reaction medium under the action of a halogen or a hydrohalic acid in particular, the latter compounds being present in the medium or introduced for this purpose.

Compounds selected from methanol, dimethyl ether, methyl acetate and methyl formate, used by themselves or in a mixture, may be mentioned as non-limiting examples of suitable precursors.

The amount of halogen-containing promoter present in the reaction mixture is advantageously less than or equal to 20%, based on the total weight of said mixture. The content of halogen-containing promoter is preferably less than or equal to 15%.

It should be noted that if the above-mentioned promoter is partially or totally introduced in the form of a precursor, the amount of precursor or promoter/precursor mixture is such as to give an amount equivalent to that mentioned above.

The process of the invention can be carried out by feeding the reactor with methanol as the only reactant in the case of carbonylation only. It can also be carried out by feeding the reactor with methyl formate in the case of an isomerization process, or with methyl formate and methanol in the case of a combined process involving simultaneous isomerization and carbonylation.

The reaction according to the invention is also carried out in the presence of water. The process according to the invention makes it possible to obtain a good productivity with low water contents, without loss of catalyst metal by precipitation.

Thus the process forming the subject of the invention can be carried out over a wide range of water concentrations in the reaction medium, but preferably with a concentration less than or equal to 14%, based on the total weight of said medium. More particularly, the water content of the reaction medium is less than or equal to 10%.

In the first variant of the process, where only the carbonylation of methanol is carried out, the water content is preferably between 2% and 8% by weight of the reaction medium.

In the second variant, where the isomerization of methyl formate is carried out, optionally simultaneously with the carbonylation of methanol, the water content is less than 5% and preferably less than 2% by weight of the reaction medium.

The process according to the invention can be carried out in the presence of iodides in a form soluble in the reaction medium. The iodides can be introduced into the reaction medium as such, but also in the form of compounds capable of forming soluble iodides.

Iodides are understood as meaning ionic species, i.e. excluding covalent iodides (such as the halogen-containing promoter in particular) and hydriodic acid.

Thus the iodides introduced as such into said mixture are selected from inorganic and organic iodides.

Inorganic iodides which may principally be mentioned are the iodides of alkaline earth metals or alkali metals, the latter being preferred. Potassium iodide, lithium iodide and sodium iodide may be mentioned among said alkali metal iodides.

Organic iodides which may be mentioned are organic compounds comprising at least one organophosphorus group and/or at least one organonitrogen group and reacting with iodine-based compounds to give ionic species containing this halogen. Examples which may be mentioned are the compounds of the formula $Q^+.I^-$, in which Q is a group $NR_4$ or $PR_4$, where R is selected from hydrogen and/or a hydrocarbon radical.

Examples which may be mentioned of compounds capable of forming iodides soluble in the reaction medium are alkali metal or alkaline earth metal carboxylates and hydroxides, such as lithium acetate, potassium hydroxide and sodium hydroxide in particular.

It should moreover be noted that the iodides may originate in ways other than those indicated above.

These compounds can thus originate from impurities, such as alkali metals or alkaline earth metals, present in the starting materials employed to prepare the catalyst solution.

Likewise the iodides can originate from the corrosion metals appearing during the reaction. It is preferable to keep the concentration threshold of these metals relatively low, of the order of a few hundred parts per million, because they have the effect especially of favoring the water-gas shift reaction and contribute to increasing the atomic ratio of iodides to iridium.

It is possible to introduce a particular amount of iodides into the reaction medium according to the amount of iridium present in the medium. Thus said amount of iodides introduced is such that the atomic ratio of iodides introduced to iridium (expressed in mol/mol) is below 10 and is kept within this range throughout the reaction.

In one preferred embodiment of the invention, the atomic ratio of iodides to iridium is kept below 3. More particularly, this ratio is below 1.5.

It has been found that the addition of such amounts of iodides makes it possible to improve the stability of the catalyst and keep the productivity of the process high.

Consequently the present invention is more particularly intended to be carried out continuously and the stable operating conditions of the process correspond to the composition and proportions indicated.

More particularly, as far as the soluble iodides are concerned, the atomic ratio of soluble iodides to iridium can be maintained by treating a mixture comprising at least the iridium compound with an ion exchange resin and then adding iodides in soluble form in an amount such that said ratio is below 10.

In addition to the compounds and reactants mentioned above, the reaction according to the invention is advantageously carried out in the presence of esters.

The ester used is preferably methyl acetate and/or methyl formate, which are used as such or in a masked form.

In one embodiment of the invention, the ester content is advantageously less than or equal to 40% by weight, based on the weight of the reaction mixture. More particularly, this content remains less than or equal to 30%.

Finally, the reaction is carried out in the presence of a solvent. The solvent used in the process according to the invention is advantageously acetic acid or formic acid. It is of course possible to use other solvents such as, in particular, compounds which are inert towards the reaction mixture and have a boiling point above that of the acid formed.

The reaction is generally carried out at a temperature between 150 and 250° C. More particularly, the reaction temperature is between 175 and 210° C. and preferably between 175 and 200° C.

The total pressure under which the reaction is carried out is generally above atmospheric pressure. More particularly, it is advantageously below $200.10^5$ Pa and preferably below or equal to $50.10^5$ Pa. In the case of a process according to the invention which involves the isomerization of methyl formate, optionally simultaneously with the carbonylation of methanol, the CO partial pressure will advantageously be between $0.1.10^5$ Pa and $25.10^5$ Pa, as indicated previously. The pressures are expressed in absolute pascals and are measured hot, i.e. under the temperature conditions of the reaction.

The process according to the invention is preferably carried out in the presence of a corrosion metal content of less than a few hundred ppm, preferably of less than 200 ppm. The corrosion metals are especially iron, nickel, chromium, molybdenum and zirconium. The corrosion metal content of the reaction mixture is maintained by the methods known to those skilled in the art, for example selective precipitation, liquid—liquid extraction or passage over ion exchange resins.

In general, the process of the invention is advantageously carried out continuously.

The reaction is carried out in equipment which is resistant to the corrosion created by the medium. Thus zirconium or alloys of the Hastelloy® C or B type are particularly suitable for the operating conditions of the reaction.

When the reaction is started, the various components are introduced into an appropriate reactor, which is fitted with stirring means so as to ensure a good homogeneity of the reaction mixture. It should be noted that although the reactor preferably comprises mechanical means for stirring the reaction mixture, it is not excluded to dispense with such means, it being possible for the mixture to be homogenized by the carbon monoxide introduced into the reactor.

It should be noted that the reaction could conveniently be carried out in a reactor of the piston type.

It is of course possible to envisage combining several reactors of the stirred and piston type.

Carbon monoxide can be introduced directly into the reactor where the reaction according to the invention takes place, but it can also be introduced into the recycling zone, which will be described below.

The reaction mixture leaving the reactor is treated in an appropriate manner for separating the products from the reaction mixture comprising especially the catalyst.

For this purpose, and in the case where the reaction is carried out continuously, it is possible for example to employ a conventional technique which consists in expanding the mixture so as to cause a partial vaporization thereof. This operation can be effected using a valve for expanding the mixture, the latter being introduced into a separator (called a flash separator). The operation can take place with or, preferably, without the provision of heat, i.e. under adiabatic conditions.

The non-vaporized part, comprising especially the catalyst which has remained in solution, is advantageously recycled to the reactor, conventionally by means of a pump.

The vaporized part, which comprises the acetic acid and/or the methyl acetate produced, is then sent to a purification zone, which conventionally comprises various distillation columns.

Finally, the process according to the invention can be carried out with the insertion of an additional reactor between the main reactor and the partial vaporization zone, more particularly upstream of the reaction mixture expansion valve; in said additional reactor, the carbon monoxide present in the dissolved and/or entrained state will be wholly or partially consumed.

The preferred conditions for carrying out such a process can be obtained directly by those skilled in the art by reference to patent FR 2 750 984, except that, according to the invention, platinum is added to the iridium.

EXAMPLES

I—Examples of the Carbonylation of Mixtures of Methyl Acetate+Methanol in the Presence of Platinum(II) Iodide Comparative Examples A, B, C, D and E and Examples 1 and 2 according to the invention A series of experiments were carried out which were identical to one another in every respect except for the nature and composition of the catalyst system. The operating conditions of these experiments are described in detail in Comparative Experiment A below and Table no. 1.

The results obtained in the various experiments are collated in Table no. 2 below, which shows:

in the column headed $V_{carb}$, the carbonylation rates calculated on the basis of the CO consumption measured in the reactor after a reaction time of 10 minutes (RT=10), corresponding to the amount of acetic acid formed by carbonylation during this period; $V_{carb}$ is expressed in mol/l.h;

in the column headed TOF (=Turnover Frequency), the ratio of the rate to the total metal concentration; TOF is expressed in $h^{-1}$.

Comparative Experiment A: Carbonylation Reaction in the Presence of Iridium by Itself First of all, the catalyst solution is prepared as follows:

Comparative Experiments B, C, D and E

Experiments no. 1 and 2 According to the Invention

These experiments are carried out under the same operating conditions and with the same initial composition of the reaction mixture except for the catalysts, the details of which are given in Table no. 1, the catalysts being introduced in the form of iridium iodide and/or rhodium iodide and/or platinum(II) iodide.

TABLE NO. 1

| | CATALYSTS | | | Observations at RT = 10 minutes | | | |
|---|---|---|---|---|---|---|---|
| EXPERIMENT | Iridium iodide (g) | Rhodium iodide (g) | Platinum iodide (g) | Total catalyst content mg/kg (ppm) | Platinum concentration (mmol/l) | Weight of reaction liquid (g) | Volume of reaction liquid (ml) |
| A (Comparative) | 0.454 | 0 | 0 | 1943 | 0.0 | 72 | 68 |
| B (Comparative) | 0.782 | 0 | 0 | 3243 | 0.0 | 74 | 70 |
| C (Comparative) | 0.256 | 0.473 | 0 | 2392 | 0.0 | 75 | 70 |
| D (Comparative) | 0 | 0 | 0.48 | 3114 | 16.2 | 67 | 66 |
| E (Comparative) | 0 | 1.2 | 0 | 3361 | 0.0 | 76 | 71 |
| 1 | 0.547 | 0 | 0.144 | 3163 | 4.7 | 73 | 68 |
| 2 | 0.454 | 0 | 0.096 | 2487 | 3.1 | 73 | 69 |

Initial composition: water = 6.4%, AcOMe = 30%, MeI = 10%, MeOH = 5.7%, catalysts according to Table, AcOH = qsp 100%, T = 190° C., P total = 30 bar

TABLE 2

| EXPERIMENT | Metal deposit in autoclave at RT = 10 minutes | Rh/Ir (mol/mol) | Ir/Pt (mol/mol) | V (carb) at RT = 10 minutes (mol/h.l) | TOF at RT = 10 minutes ($h^{-1}$) |
|---|---|---|---|---|---|
| A (Comparative) | Light deposit | 0/100% | 100/0% | 11 | 1030 |
| B (Comparative) | Deposit | 0/100% | 100/0% | 18 | 1010 |
| C (Comparative) | Deposit | 70/30% | 100/0% | 17 | 860 |
| D (Comparative) | Heavy deposit | 0/0% | 0/100% | 0 | 0 |
| E (Comparative) | Heavy deposit | 100/0% | 0/0% | 16.5 | 470 |
| 1 | No deposit | 0/100% | 73/27% | 21 | 1190 |
| 2 | Traces of deposit | 0/100% | 75/25% | 10 | 730 |

The following are introduced into a 100 ml HASTELOY® B2 autoclave:

0.454 g of iridium iodide, 10 g of acetic acid, 1 g of water.

The autoclave is then placed under a carbon monoxide absolute pressure of 6 bar at room temperature.

The temperature is raised to 190° C.

The preparation of the catalyst solution takes 25 minutes.

The carbonylation reaction is carried out as follows:

Acetic acid, methyl iodide, water, methanol and methyl acetate are injected into the autoclave under CO pressure.

The initial composition of the reaction mixture is as follows (by weight):

water: 6.4% methyl acetate: 30% methyl iodide: 10% methanol: 5.7% iridium: 1943 ppm acetic acid: qsp 100%

The total absolute pressure is kept constant at 30 bar by injecting carbon monoxide.

The temperature is maintained at 190° C.±0.5° C.

After the reaction, the reaction liquid weighs 72 g.

The carbonylation rate ($V_{carb}$) is 11 mol/l/h.

TOF is 1030 $h^{-1}$.

After the reaction, a light metal deposit is observed in the autoclave.

As is clearly apparent from Table 2, all the experiments described above demonstrate the following points:

Platinum by itself, in the form of platinum(II) iodide, $PtI_2$, has no catalytic action in the carbonylation of methanol (Experiment D).

When used in a sufficient amount and in appropriate proportions relative to the iridium (Experiment 1), platinum increases the catalytic activity of the iridium in the carbonylation of methanol, compared with rhodium by itself (Experiment E), iridium by itself (Experiments A and B) and iridium+rhodium (Experiment C).

Experiment 2, which was not carried out under the optimum conditions of the invention (Pt=3,1 mmol/l), nevertheless shows an improvement in the stability of the catalyst.

The remarkable stability of the catalysts in Experiment no. 1 according to the invention, since no metal deposit of iridium and/or platinum is observed.

Table no. 2 clearly demonstrates the improvement in the carbonylation rate for a sufficient platinum content in the catalyst system and an appropriate atomic ratio of iridium to platinum.

II—Examples of the Carbonylation of Methyl Acetate in the Presence of Tetraiododicarbonyldiplatinum, $[PtI_2(CO)]_2$ Experiments 3, 4, 5 and 6 According to the Invention Comparative Experiments F and G A series of experiments were carried out which were identical to one another in every respect except for the nature and composition of the catalyst system. The operating conditions of these experiments are described in detail in Comparative Experiment G below and Table no. 3.

The results obtained in the various experiments are collated in Table no. 4, which shows:
- in the column headed $V_{carb}$, the carbonylation rates calculated on the basis of the CO consumption measured in the reactor for given concentrations of methyl acetate—AcOMe—of 20% and 15% by weight in the reaction mixture, corresponding to the amount of acetic acid formed by carbonylation; $V_{carb}$ is expressed in mol/l.h;
- in the column headed TOF (=Turnover Frequency), the ratio of the rate to the total metal concentration; TOF is expressed in $h^{-1}$.

Comparative Experiment G: Carbonylation Reaction in the Presence of Iridium by Itself First of all, the catalyst solution is prepared as follows:
The following are introduced into a 100 ml HASTELLOY® B2 autoclave:
0.4596 g of iridium iodide,
10 g of acetic acid,
1 g of water.

The autoclave is then placed under a carbon monoxide absolute pressure of 6 bar at room temperature.
The temperature is raised to 190° C.
The preparation of the catalyst solution takes 25 minutes.
The carbonylation reaction is carried out as follows:
Acetic acid, methyl iodide, water and methyl acetate are injected into the autoclave under CO pressure.
The initial composition of the reaction mixture is as follows (by weight):

| | |
|---|---|
| water: | 6.4% |
| methyl acetate: | 30% |
| methyl iodide: | 10% |

| -continued | |
|---|---|
| methanol: | 0% |
| iridium: | 2587 ppm |
| acetic acid: | qsp 100% |

The total absolute pressure is kept constant at 30 bar by injecting carbon monoxide.
The temperature is maintained at 190° C.±0.5° C.
After the reaction, the reaction liquid weighs 52.3 g.
The carbonylation rate ($V_{carb}$) is 16 mol/l/h and 14 mol/l/h, respectively, for 20% and 15% by weight of AcOMe.
The corresponding values of TOF are 1110 and 970 $h^{-1}$.
After the reaction, a metal deposit is observed in the autoclave.

Comparative Experiment F
Experiments no. 3, 4, 5 and 6 According to the Invention These experiments are carried out under the same operating conditions and with the same initial composition of the reaction mixture except for the catalysts, the details of which are given in Table no. 3, the catalysts being introduced in the form of iridium iodide and tetraiododicarbonyldiplatinum, $[PtI_2(CO)]_2$.

TABLE NO. 3

| | CATALYSTS | | | Observations at RT = 10 minutes | | | |
|---|---|---|---|---|---|---|---|
| EXPERIMENT | Iridium iodide (g) | Rhodium iodide (g) | $[PtI_2(CO)]_2$ (g) | Total catalyst content (ppm) | Pt concentration (mmol/l) | Weight of reaction liquid (g) | Volume of reaction liquid (ml) |
| F (Comparative) | 0 | 0 | 0.1662 | 1399 | 7.6 | 48.6 | 46 |
| G (Comparative) | 0.4596 | 0 | 0 | 2587 | 0.0 | 52.3 | 49 |
| 3 | 0.3899 | 0 | 0.2491 | 4143 | 10.9 | 52.3 | 48 |
| 4 | 0.4600 | 0 | 0.1662 | 3989 | 7.3 | 51.0 | 48 |
| 5 | 0.5001 | 0 | 0.0844 | 3429 | 3.6 | 53.0 | 49 |
| 6 | 0.2784 | 0 | 0.4134 | 4894 | 18.1 | 51.3 | 48 |

Initial composition: water = 6.4%, AcOMe = 30%, MeI = 10%, MeOH = 0%, catalysts according to Table, AcOH = qsp 100%, T = 190° C., P total = 30 bar

TABLE NO. 4

| EXPERIMENT | Metal deposit in autoclave at RT = 10 minutes | Rh/Ir (mol/mol) | Ir/Pt (mol/mol) | $V_{(carb)}$ at 20% [AcOMe] (mol/h.l) | TOF at 20% [AcOMe] (hour$^{-1}$) | $V_{(carb)}$ at 15% [AcOMe] (mol/h.l) | TOF at 15% [AcOMe] (hour$^{-1}$) |
|---|---|---|---|---|---|---|---|
| F (Comparative) | Heavy deposit | 0/0% | 0/100% | | | 2.5 (at RT = 10) | 330 (at RT = 10) |
| G (Comparative) | Deposit | 0/100% | 100/0% | 16 | 1110 | 14 | 970 |
| 3 | No deposit | 0/100% | 53/47% | 33 | 1410 | 24 | 1030 |
| 4 | No deposit | 0/100% | 67/33% | 35 | 1600 | 29.5 | 1340 |
| 5 | No deposit | 0/100% | 81/19% | 31 | 1610 | 24 | 1250 |
| 6 | No deposit | 0/100% | 33/67% | 24 | 890 | 20 | 740 |

All the experiments described above demonstrate the following points:

Platinum by itself, employed in the form of tetraiododicarbonyldiplatinum, $[(PtI_2(CO)]_2$, has a valuable catalytic action in terms of TOF (Experiment F=330 $h^{-1}$) compared with platinum by itself in non-carbonylated form (Experiment D=0 $h^{-1}$).

When used in association with iridium (Experiments no. 3, 4 and 5 according to the invention) in a sufficient amount and in appropriate proportions relative to the iridium, platinum in the form of tetraiododicarbonyldiplatinum, $[PtI_2(CO)]_2$, increases the activity of the iridium in the carbonylation of methyl acetate, compared with iridium by itself (Comparative Experiment G).

Experiment 6, which was not carried out under the optimum conditions of the invention (Ir/Pt=0.5), nevertheless shows an improvement in the stability of the catalyst.

The remarkable stability of the catalysts in Experiments no. 3, 4 and 5 according to the invention, since no metal deposit of platinum and/or iridium is observed.

Table no. 4 clearly demonstrates the improvement in the carbonylation rate for a sufficient platinum content in the catalyst system and an appropriate atomic ratio of iridium to platinum.

What is claimed is:

1. A process for the preparation of acetic acid, methyl acetate or both acetic acid and methyl acetate in a liquid phase reaction medium comprising isomerization of methyl formate and optionally carbonylation of methanol, in the presence of water, a solvent, a homogeneous catalyst system comprising iridium and a halogen-containing promoter, and carbon monoxide, wherein said catalyst system also comprises platinum.

2. The process as claimed in claim 1, wherein said process is a process of isomerization of methyl formate wherein a carbon monoxide partial pressure of between $0.1.10^5$ Pa and $25.10^5$ Pa is maintained throughout the reaction.

3. The process as claimed in claim 1 wherein said reaction comprises a simultaneous methanol carbonylation reaction and a methyl formate isomerization reaction, wherein said reaction is carried out under a carbon monoxide partial pressure of between $0.1.10^5$ Pa and $25.10^5$ Pa throughout the reaction.

4. The process as claimed in claim 1, wherein the platinum is introduced into said catalyst system in the form of metallic platinum, a platinum salt or an oxide.

5. The process as claimed in claim 1, wherein the platinum is introduced into the catalyst system in the form of a coordination complex.

6. The process as claimed in claim 5, wherein the coordination complex is a coordination complex of platinum with at least one ligand selected from the group consisting of carbon monoxide, a carbon monoxide/halogen combination, organonitrogen compounds and organophosphorus compounds.

7. The process as claimed in claim 5, wherein said complex is $[PtI_2(CO)]_2$.

8. The process as claimed in claim 4, wherein the platinum concentration of at least 4 mmol/l of reaction medium and an atomic ratio of iridium to platinum of between 2 and 5 are maintained.

9. The process as claimed in claim 5, wherein a platinum content of at least 1 mmol/l of reaction medium and an atomic ratio of iridium to platinum of between 1 and 5 are maintained.

10. The process as claimed in claim 1, wherein said catalyst system also contains rhodium.

11. The process as claimed in claim 10, wherein rhodium and iridium are maintained in an atomic ratio of rhodium to iridium of between 0.01 and 99.

12. The process as claimed in claim 10, wherein a concentration of iridium and rhodium in the reaction medium of between 0.1 and 100 mmol/l is maintained.

13. The process as claimed in claim 10, wherein the platinum is introduced into the catalyst system in the form of metallic platinum, a platinum salt or a platinum oxide, and a platinum content of at least 4 mmol/l of reaction medium and an atomic ratio of (iridium+rhodium) to platinum of between 2 and 5 are maintained.

14. The process as claimed in claim 10, wherein the platinum is introduced in the form of a coordination complex, and a platinum content of at least 1 mmol/l of reaction medium and an atomic ratio of (iridium+rhodium) to platinum of between 1 and 5 are maintained.

15. The process as claimed in claim 1, wherein a concentration of iridium in the reaction medium of between 0.1 and 100 mmol/l is maintained.

16. The process as claimed in claim 15, wherein a concentration of iridium in the reaction medium of between 1 and 20 mmol/l, is maintained.

17. The process as claimed in claim 1 which is carried out in the presence of a water content less than or equal to 14% by weight of the reaction medium.

18. The process as claimed in claim 17, which is carried out in the presence of a water content less than or equal to 10% by weight of the reaction medium.

19. The process as claimed in claim 18, in which the reaction medium contains water in an amount of less than 5% by weight.

20. The process as claimed in claim 19, wherein the reaction medium contains water in an amount of less than 2% by weight.

21. The process as claimed in claim 1, wherein said halogen-containing promoter comprises an elemental halogen or a halogen in a compound with hydrogen or a methyl or acetyl radical.

22. The process as claimed in claim 21, wherein said halogen-containing promoter is methyl iodide.

23. The process as claimed in claim 1, which is carried out in the presence of a halogen-containing promoter in an amount of less than or equal to 20% by weight of the reaction medium.

24. The process as claimed in claim 23, which is carried out in the presence of a halogen-containing promoter in an amount of less than or equal to 15% by weight of the reaction medium.

25. The process as claimed in claim 1, which is carried out in the presence of an ester in an amount of less than 40% by weight of the reaction medium.

26. The process as claimed in claim 25, which is carried out in the presence of an ester in an amount of less than 30% by weight of the reaction medium.

27. The process as claimed in claim 1, wherein iodides are introduced into the reaction medium in an amount sufficient to maintain an atomic ratio of soluble iodides introduced into the reaction medium to iridium of less than 10.

28. The process as claimed in claim 1, which is carried out continuously.

29. A process for the preparation of acetic acid, methyl acetate or both acetic acid and methyl acetate by a reaction of carbonylation of methanol in a liquid phase reaction medium in the presence of water, a solvent, a homogeneous catalyst system comprising iridium and a halogen-containing promoter, and carbon monoxide, wherein said catalyst system also comprises platinum.

30. The process as claimed in claim 29, wherein a carbon monoxide partial pressure of between $0.1.10^5$ Pa and $200.10^5$ Pa is maintained throughout the reaction.

31. The process as claimed in claim 29, wherein the platinum is introduced into said catalyst system in the form of metallic platinum, a platinum salt or an oxide.

32. The process as claimed in claim 29, wherein the platinum is introduced into the catalyst system in the form of a coordination complex.

33. The process as claimed in claim 32, wherein the coordination complex is a coordination complex of platinum with at least one ligand selected from the group consisting of carbon monoxide, a carbon monoxide/halogen combination, organonitrogen compounds and organophosphorus compounds.

34. The process as claimed in claim 32, wherein said complex is $[PtI_2(CO)]_2$.

35. The process as claimed in claim 31, wherein the platinum concentration of at least 4 mmol/l of reaction medium and an atomic ratio of iridium to platinum of between 2 and 5 are maintained.

36. The process as claimed in claim 32, wherein a platinum content of at least 1 mmol/l of reaction medium and an atomic ratio of iridium to platinum of between 1 and 5 are maintained.

37. The process as claimed in claim 29, wherein said catalyst system also contains rhodium.

38. The process as claimed in claim 37, wherein rhodium and iridium are maintained in an atomic ratio of rhodium to iridium of between 0.01 and 99.

39. The process as claimed in claim 37, wherein a concentration of iridium and rhodium in the reaction medium of between 0.1 and 100 mmol/l is maintained.

40. The process as claimed in claim 37, wherein the platinum is introduced into the catalyst system in the form of metallic platinum, a platinum salt or a platinum oxide, and a platinum content of at least 4 mmol/l of reaction medium and an atomic ratio of (iridium+rhodium) to platinum of between 2 and 5 are maintained.

41. The process as claimed in claim 37, wherein the platinum is introduced in the form of a coordination complex, and a platinum content of at least 1 mmol/l of reaction medium and an atomic ratio of (iridium+rhodium) to platinum of between 1 and 5 are maintained.

42. The process as claimed in claim 29, wherein a concentration of iridium in the reaction medium of between 0.1 and 100 mmol/l is maintained.

43. The process as claimed in claim 42, wherein a concentration of iridium in the reaction medium of between 1 and 20 mmol/l, is maintained.

44. The process as claimed in claim 29, which is carried out in the presence of a water content less than or equal to 14% by weight of the reaction medium.

45. The process as claimed in claim 44, which is carried out in the presence of a water content less than or equal to 10% by weight of the reaction medium.

46. The process as claimed in claim 44, wherein the reaction medium contains water in an amount of between 2 and 8% by weight.

47. The process as claimed in claim 29, wherein said halogen-containing promoter comprises an elemental halogen or a halogen in a compound with hydrogen or a methyl or acetyl radical.

48. The process as claimed in claim 47, wherein said halogen-containing promoter is methyl iodide.

49. The process as claimed in claim 29, which is carried out in the presence of a halogen-containing promoter in an amount of less than or equal to 20% by weight of the reaction medium.

50. The process as claimed in claim 49, which is carried out in the presence of a halogen-containing promoter in an amount of less than or equal to 15% by weight of the reaction medium.

51. The process as claimed in claim 29, which is carried out in the presence of an ester in an amount of less than 40% by weight of the reaction medium.

52. The process as claimed in claim 51, which is carried out in the presence of an ester in an amount of less than 30% by weight of the reaction medium.

53. The process as claimed in claim 29, wherein iodides are introduced into the reaction medium in an amount sufficient to maintain an atomic ratio of soluble iodides introduced into the reaction medium to iridium of less than 10.

54. The process as claimed in claim 29, which is carried out continuously.

* * * * *

UNITED STATES PATENT AND TRADEMARK OFFICE
CERTIFICATE OF CORRECTION

PATENT NO. : 6,916,952 B1
DATED : July 12, 2005
INVENTOR(S) : Carol Le Berre et al.

It is certified that error appears in the above-identified patent and that said Letters Patent is hereby corrected as shown below:

Title page,
Item [75], Inventors, change "La Croix-Falfgarde" to -- La Croix-Falgarde --;

Column 1,
Line 41, change "WO 97/135829" to -- WO 97/35829 --.

Signed and Sealed this

First Day of November, 2005

JON W. DUDAS
*Director of the United States Patent and Trademark Office*